United States Patent [19]

Johns

[11] Patent Number: 4,616,660
[45] Date of Patent: Oct. 14, 1986

[54] VARIABLE ALTERNATING CURRENT OUTPUT NERVE LOCATOR/STIMULATOR

[75] Inventor: David L. Johns, Clearwater, Fla.

[73] Assignee: Suncoast Medical Manufacturing, Inc., Clearwater, Fla.

[21] Appl. No.: 680,007

[22] Filed: Dec. 10, 1984

[51] Int. Cl.⁴ ............................................. A61B 15/05
[52] U.S. Cl. .................................................. 128/741
[58] Field of Search ................ 128/741, 303.1, 303.18, 128/362

[56] References Cited

U.S. PATENT DOCUMENTS

| | | | |
|---|---|---|---|
| 1,548,184 | 8/1925 | Cameron | 128/423 |
| 2,437,697 | 4/1946 | Kalom | 128/737 |
| 2,949,107 | 8/1960 | Ziegler | 128/303.13 |
| 3,128,759 | 4/1964 | Bellis | 433/32 |
| 3,207,151 | 9/1965 | Takagi | 128/734 |
| 3,368,557 | 2/1968 | Hassing et al. | 604/92 |
| 3,682,162 | 8/1972 | Colver | 128/741 |
| 3,830,226 | 8/1974 | Staub et al. | 128/741 |
| 4,099,519 | 7/1978 | Warren | 128/741 |
| 4,157,087 | 6/1979 | Miller et al. | 128/741 |
| 4,515,168 | 5/1985 | Chester et al. | 128/741 |

Primary Examiner—Kyle L. Howell
Assistant Examiner—David Shay
Attorney, Agent, or Firm—A. W. Fisher, III

[57] ABSTRACT

A variable alternating current output nerve locator/stimulator comprising a hollow substantially cylindrical enclosure configured to operatively house a direct current power source electrically coupled to a current power convertor including circuitry to convert the direct current to alternating current electrically coupled to a current regulator, a nerve probe electrically coupled to the current regulator and a ground electrically coupled to the direct current power source, a removable nerve probe cover and a removable ground cover removably attached to opposite ends of the hollow substantially cylindrical enclosure to permit selective withdrawal of the ground from the hollow substantially cylindrical enclosure and application of the nerve probe to the patient after adjustment of the current regulator to control the alternating current from the direct current power source.

1 Claim, 2 Drawing Figures

VARIABLE ALTERNATING CURRENT OUTPUT NERVE LOCATOR/STIMULATOR

BACKGROUND OF THE INVENTION

1. Field of the Invention

A variable alternating current output nerve locator/stimulator including a nerve probe and ground disposed at opposite ends thereof wherein the ground may be selectively withdrawn from the housing.

2. Description of the Prior Art

Numerous nerve locators/stimulators have been designed for medical uses involving identification and monitoring of motor nerves including long thoracic nerves and chest, hand and joint surgery, as well as head and neck surgery. Unfortunately, many such devices are unsatisfactory because of large size, operational complexity, cost of manufacturing and difficulty in use. Furthermore, it is desirable to be able to vary the amount of electrical energy output of the nerve locator.

Examples of the prior art are shown in U.S. Pat. Nos. 1,548,184; 2,437,697; 2,949,107; 3,128,759; 3,207,151; 3,664,329; 3,830,226; 4,011,624; and Germany Pat. No. 179,379.

Accordingly, it can be seen that there is a real need for a hand-held nerve locator/stimulator device including means to easily varying an alternating current energy output thereof.

SUMMARY OF THE INVENTION

The present invention relates to a variable alternating current output nerve locator/stimulator comprising a hollow enclosure having a removable nerve probe cover and removable ground cover removably attached to opposite ends thereof.

The hollow enclosure is configured to operatively house a direct current power source, a direct current to alternating current power converter, and a current regulator. In addition, a nerve probe and ground are disposed in opposite ends of the hollow enclosure.

The nerve probe includes an insulating retainer having a channel formed therethrough to operatively receive a nerve probe member. The nerve probe member comprises a nerve probe element having a first and second element and an insulating cover. The inner portion of the nerve probe member is operatively housed and secured by the nerve probe retainer.

The ground comprises a ground element, a major portion of which is encased in insulating element having a hand held element affixed to the inner portion thereof. Extending rearwardly from the hand held element is a retainer element configured to be operatively received within a retainer member including aperture to press fit therebetween. Electrically coupled to an extension is a flexible insulated conductor electrically connected to the voltage source.

In use, the operator determines and sets the required current output by adjusting the current regulator. The current output selected is indicated by an index formed on the current regulator. The operator then inserts the ground element into living subcutaneous tissue. The operator next inserts the first element of the nerve probe member into an incision to locate and/or stimulate a nerve controlling a motor muscle. When the first element is touched to exposed nerve tissues, contraction of the normally innervated muscle will occur.

The invention accordingly comprises the features of construction, combination of elements and arrangement of parts which will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
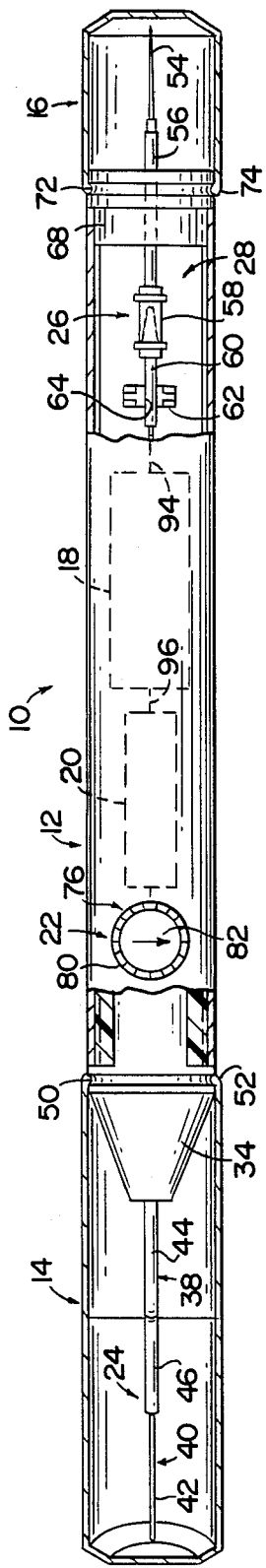
FIG. 1 is a top cross-sectional view of the variable alternating current output nerve locator/stimulator.
Figure 2:
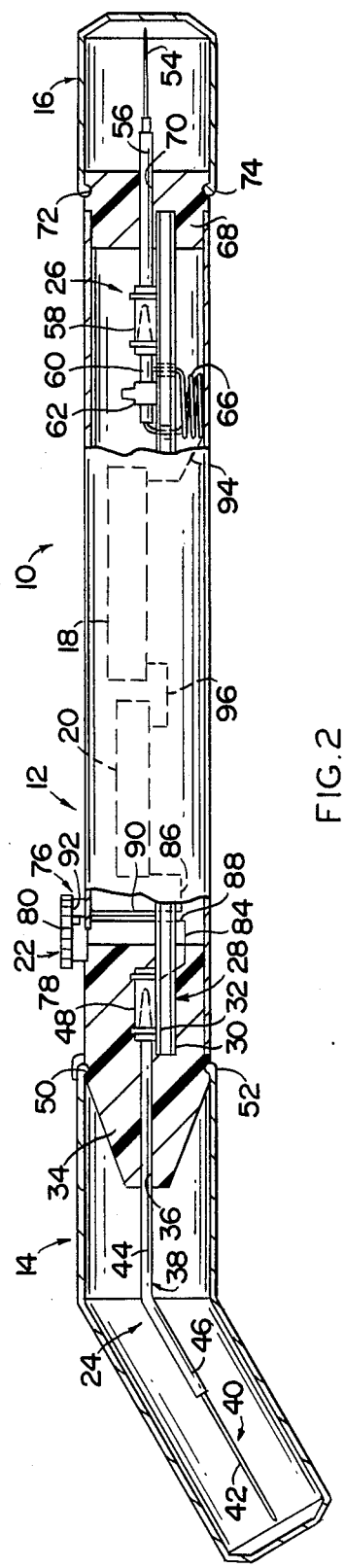
FIG. 2 is a partial cross-sectional side view of the variable alternating current output nerve locator/stimulator.

As shown in FIGS. 1 and 2, the present invention relates to a variable alternating current output nerve locator/stimulator generally indicated as 10. The variable alternating current output nerve locator/stimulator 10 comprises a hollow substantially cylindrical enclosure 12 having a removable nerve probe cover and removable ground cover generally indicated as 14 and 16 respectively removably attached to opposite ends thereof.

As best shown in FIGS. 1 and 2, the hollow substantially cylindrical enclosure 12 is configured to operatively house a direct current power source generally indicated as 18, a direct current to alternating current power converter generally indicated as 20 and a current regulator generally indicated as 22. In addition, a nerve probe and ground generally indicated as 24 and 26 respectively are disposed in opposite ends of the hollow substantially cylindrical casing 12.

As best shown in FIG. 2, the variable alternating current output nerve locator/stimulator 10 includes a printed circuit board generally indicated as 28 retained within the hollow substantially cylindrical enclosure 12 by a pair of substantially parallel retainers or guides indicated as 30 and 32. The printed circuit board 28 includes circuitry comprising the alternating current power converter 20 and current regulator 22, as well as operatively supporting the direct current voltage source 18.

As shown in FIGS. 1 and 2, the nerve probe 24 includes an insulating retainer 34 having a channel 36 formed therethrough to operatively receive the nerve probe member generally indicated as 38. The nerve probe member 38 comprises a nerve probe element 40 having a first and second element 42 and 44 and an insulating cover 46. The inner portion of the nerve probe member 38 is operatively housed and secured by nerve probe retainer 48 attached to the printed circuit board guide 32 in operatively electrical relationship relative to the current regulator 22 as more fully described hereinafter. The insulating retainer 34 is substantially conical in shape and includes a peripheral annular groove 50 formed on the inner portion thereof to receive an annular rim or locking member 52 formed on the removable nerve probe cover 14.

The ground 26 comprises a ground element 54, a portion of which is encased in insulating element 56 having a hand held element 58 affixed to the inner portion thereof. Extending rearwardly from the hand held element 58 is a male retainer element 60 configured to be operatively received within female retainer member 62 including aperture 64 to press fit therebetween. Electrically coupled to the ground element 54 through the insulating member 56 is a flexible insulated conductor 66 electrically connected to the voltage source 18. The retainer member 62 is fixedly attached to the upper guide 32. The ground 26 further includes an adapter 68 including a channel 70 having an annular retainer member 72 to receive retainer rib 74 formed on the inner portion of the removable ground cover 16.

The current regulator 22 comprises a switch member 76 including a post 78 supported on the printed circuit board 28 having a rotatable control member 80 affixed to the outer portion thereof, external to the hollow substantially cylindrical enclosure 12. A visual index or indicia 82 is formed on the outer surface of the rotatable control member 80 to provide a visual indication of the current settings selected by the operator. The current regulator 22 is electrically coupled between the nerve probe 24 and alternating current power converter 20 by conductors 84 and 86 respectively coupled to switch conductors 88 and 90 respectively disposed with the post 78 to vary the selected output by rotation of the rotatable control member 80 having conductive surface 92 formed thereon.

The voltage source 18 is coupled to the flexible insulator conductor 66 and direct current to alternating current connector 20 by conductors 94 and 96 respectively.

In use, the operator determines the required current output required for the particular application and sets the preselected current output by rotating the rotatable control member 80. The relative current output selected is indicated by the indicia 82 formed on the control member 80. Once the desired output is selected, the operator withdraws the ground element 54 from the female retainer member 62 allowing the flexible insulated conductor 66 to payout of the hollow substantially cylindrical enclosure 12 and inserts the ground element 54 into living subcutaneous tissue. The operator then inserts the nerve probe element 40 into an incision to locate and/or stimulate a nerve controlling a motor muscle. When the nerve probe element 40 is touched to the exposed nerve tissues, contraction of the normally innervated muscle will occur.

It will thus be seen that the objects set forth above, and those made apparent from the preceeding description are efficiently attained and since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statement of the scope of the invention which as a matter of language, might be said to fall therebetween.

Now that the invention has been described,
What is claimed is:

1. A variable alternating current output nerve locator/stimulator comprising a hollow enclosure which houses a direct current power source electrically coupled to a current power convertor, said current power convertor including circuit means to convert direct current to alternating current electrically coupled to a current regulator, a nerve probe electrically coupled to said current regulator and a ground electrically coupled to said direct current power source, said ground comprising a ground element partially encased within an insulating element and a retainer element extending from said ground element operatively receivable including an aperture disposed within said hollow enclosure said aperture receiving said retainer element therein selectively retaining said ground within said hollow enclosure, a removable nerve probe cover and a removable ground cover removably attached to opposite ends of said hollow enclosure, said ground element being electrically coupled to a flexible insulated conductor electrically connected to said voltage source, said conductor permitting selective withdrawal of said ground element and a desired portion of said flexible insulated conductor from said hollow enclosure when said removable ground cover is removed from said hollow enclosure and application of said nerve probe to the patient after adjustment of said current regulator to control the alternating current output from said direct current power source when said removable nerve probe cover is removed from said hollow enclosure.

* * * * *